(12) United States Patent
Li et al.

(10) Patent No.: US 11,781,076 B2
(45) Date of Patent: Oct. 10, 2023

(54) MULTI-TUBE REACTOR SYSTEMS AND PROCESSES FOR NO-OXIDATIVE CONVERSION OF METHANE

(71) Applicant: CHEVRON U.S.A. INC., San Ramon, CA (US)

(72) Inventors: Lin Li, San Ramon, CA (US); Huping Luo, San Ramon, CA (US); Xiaoying Ouyang, San Ramon, CA (US); Alexander Kuperman, San Ramon, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 17/683,990

(22) Filed: Mar. 1, 2022

(65) Prior Publication Data
US 2023/0279301 A1  Sep. 7, 2023

(51) Int. Cl.
*C10G 50/00* (2006.01)
*C10G 47/34* (2006.01)

(52) U.S. Cl.
CPC ............. *C10G 50/00* (2013.01); *C10G 47/34* (2013.01); *C10G 2300/1025* (2013.01);
(Continued)

(58) Field of Classification Search
CPC ................ C10G 50/00; C10G 47/34; C10G 2300/1025; C10G 2400/20; C10G 2400/22; C10G 2400/30
See application file for complete search history.

(56) References Cited

U.S. PATENT DOCUMENTS

| 4,652,687 A | * | 3/1987 | Imai | ............... C07C 5/321 585/443 |
| 5,202,517 A | * | 4/1993 | Minet | ............... C07C 5/3335 585/920 |

(Continued)

OTHER PUBLICATIONS

Zamaro et al., Zeolite washcoating onto Cordierite honeycomb reactors for environmental applications, Chemical Engineering Journal, vol. 106, pp. 25-33, 2005.

(Continued)

*Primary Examiner* — In Suk C Bullock
*Assistant Examiner* — Jason Y Chong
(74) *Attorney, Agent, or Firm* — Hunton Andrews Kurth LLP

(57) ABSTRACT

The present disclosure refers to systems and methods for efficiently converting a $C_1$-$C_3$ alkane such as natural gas to a liquid $C_2$-$C_{10}$ product and hydrogen. Generally, the process comprises flowing the $C_1$-$C_3$ alkane through a plurality of tubes within a vessel wherein the tubes house a catalyst for converting the $C_1$-$C_3$ alkane to the liquid $C_2$-$C_{10}$ product and hydrogen. The $C_1$-$C_3$ alkane is heated under suitable conditions to produce the liquid $C_2$-$C_{10}$ product and hydrogen. Advantageously, the $C_1$-$C_3$ alkane is heated by burning a fuel outside the tubes in fuel burning nozzles configured to transfer heat from the burning through the tubes.

15 Claims, 2 Drawing Sheets

Multi-tube reactor with top-fired heater

(52) U.S. Cl.
CPC ..... *C10G 2400/20* (2013.01); *C10G 2400/22* (2013.01); *C10G 2400/30* (2013.01)

(56) References Cited

U.S. PATENT DOCUMENTS

| | | | |
|---|---|---|---|
| 5,389,342 A * | 2/1995 | Savage | B01J 8/062 |
| | | | 422/111 |
| 2002/0103402 A1* | 8/2002 | Chang | C07C 27/16 |
| | | | 568/910.5 |
| 2010/0312029 A1 | 12/2010 | Gulotty, Jr. | |
| 2011/0060176 A1 | 3/2011 | Kiesslich et al. | |
| 2012/0165418 A1* | 6/2012 | Park | B01J 23/002 |
| | | | 518/713 |
| 2016/0074844 A1* | 3/2016 | Freer | B01J 23/10 |
| | | | 502/201 |
| 2016/0289141 A1 | 10/2016 | Bachmann et al. | |
| 2016/0362351 A1* | 12/2016 | Nagaki | B01J 23/745 |
| 2017/0007989 A1 | 1/2017 | Coelho Tsou et al. | |
| 2021/0115341 A1 | 4/2021 | Sampath | |
| 2021/0309589 A1* | 10/2021 | Yun | C10G 50/00 |

OTHER PUBLICATIONS

Aboul-Gheit et al., Oxygen free conversion of natural gas to useful hydrocarbons and hydrogen over monometallic Mo and Bimetalli Mo-Fe, Mo-Co or Mo-Ni/HZSM-5 catalysts prepared by mechanical mixing, Fuel Processing Technology, vol. 102, pp. 24-29, May 14, 2012.
International Search REport and Written Opinion dated Jun. 16, 2023 issued in PCT/US2023/14280.

* cited by examiner

Figure 1 Reaction temperature and equilibrium conversion for methane to benzene reaction

Multi-tube reactor with top-fired heater

MULTI-TUBE REACTOR SYSTEMS AND PROCESSES FOR NO-OXIDATIVE CONVERSION OF METHANE

FIELD OF THE DISCLOSURE

The present disclosure relates to systems and methods for converting a $C_1$-$C_3$ alkane to a liquid $C_2$-$C_{10}$ product and hydrogen.

BACKGROUND AND SUMMARY

Hydrogen is one of the more important options for future clean energy. In addition, higher molecular weight hydrocarbons such as olefins and aromatics are often desirable as value added chemicals. While methane has been used to make such value added chemicals in the past the process are usually not cost-effective. What is needed is a solution that produces hydrogen and value added chemicals in a cost-effective manner. It would further be advantageous if such a solution was not energy intensive.

Advantageously, the instant application pertains to new systems and methods that advantageously produce hydrogen and value added chemicals in a cost-effective manner and are not energy intensive.

In one embodiment the application pertains to a process for converting a $C_1$-$C_3$ alkane to a liquid $C_2$-$C_{10}$ product and hydrogen. The process comprises flowing the $C_1$-$C_3$ alkane through a plurality of tubes within a vessel wherein the tubes house a catalyst for converting the $C_1$-$C_3$ alkane to the liquid $C_2$-$C_{10}$ product and hydrogen. The $C_1$-$C_3$ alkane is heated under suitable conditions to produce the liquid $C_2$-$C_{10}$ product and hydrogen. The $C_1$-$C_3$ alkane is heated by burning a fuel outside the tubes in fuel burning nozzles configured to transfer heat from the burning through the tubes.

In another embodiment the application pertains to a process for converting natural gas to a liquid $C_2$-$C_{10}$ product comprising ethylene, benzene, naphthalene, or a mixture thereof and hydrogen. The process comprises flowing the natural gas through a plurality of tubes within a vessel wherein the tubes house a catalyst for converting the natural gas to the liquid $C_2$-$C_{10}$ product comprising ethylene, benzene, naphthalene, or a mixture thereof and hydrogen. The natural gas is heated at a temperature of from about 500, or from about 700, up to about 1000 or up to about 1200° C., and a pressure of from about 1 atmosphere up to about 3, or up to about 5, or up to about 10, or up to about 20 atmospheres to produce the liquid $C_2$-$C_{10}$ product comprising ethylene, benzene, naphthalene, or a mixture thereof and hydrogen. The natural gas is heated by burning a fuel outside the tubes in fuel burning nozzles configured to transfer heat from the burning through the tubes. Additionally or alternatively, electric or other heating may be employed with the burning fuel or in place of it.

In another embodiment the application pertains to a reactor for conversion of alkanes to liquid hydrocarbons and hydrogen. The reactor comprises a vessel and a plurality of tubes within the vessel wherein the tubes are configured to house a catalyst. The vessel is configured to burn a fuel outside the plurality of tubes. The vessel is further configured to transfer heat from the burning fuel to the catalyst housed within the plurality of tubes.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Various embodiments of the present disclosure, together with further objects and advantages, may best be understood by reference to the following description taken in conjunction with the accompanying drawings.

DETAILED DESCRIPTION

Figure 1:
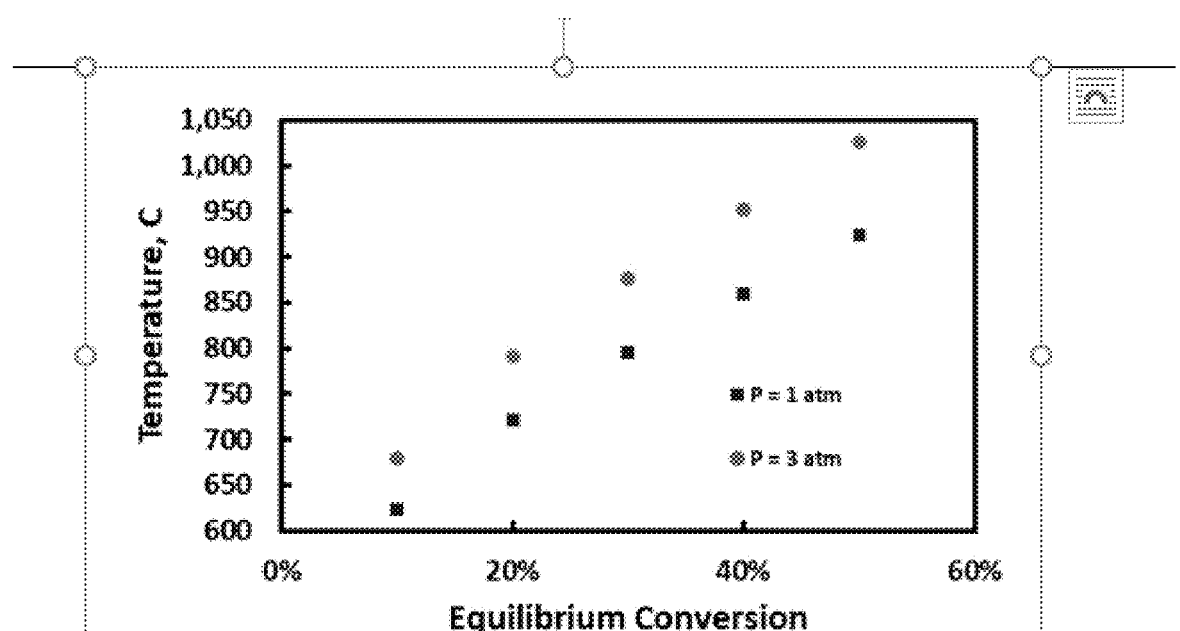
FIG. 1 shows reaction temperature, pressure, and equilibrium conversion for a methane to benzene reaction.

The following description of embodiments provides a non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

General Process

The instant application pertains to a process for converting a $C_1$-$C_3$ alkane to a liquid $C_2$-$C_{10}$ product and hydrogen. The process generally comprises first flowing the $C_1$-$C_3$ alkane through a plurality of tubes within a vessel. The tubes typically house a catalyst for converting the $C_1$-$C_3$ alkane to the liquid $C_2$-$C_{10}$ product and hydrogen. The $C_1$-$C_3$ alkane is not particularly limited and may include, for example, natural gas, methane, ethane, propane, or mixtures thereof. As used herein natural gas comprises methane and potentially higher alkanes, carbon dioxide, nitrogen or other gases, and/or sulfide compounds such as hydrogen sulfide, and mixtures thereof. The produced product typically comprises liquid $C_2$-$C_{10}$ product and hydrogen. The liquid $C_2$-$C_{10}$ product is not particularly limited and could be saturated, unsaturated, aromatic, or a mixture of such compounds. In some embodiments the liquid $C_2$-$C_{10}$ product may comprise ethylene, benzene, naphthalene, and various mixtures thereof depending upon the desired products and reactions used.

The $C_1$-$C_3$ alkane is usually heated under suitable conditions in the presence of the catalyst to produce the liquid $C_2$-$C_{10}$ product and hydrogen. Suitable conditions may vary depending upon the reactants, desired products, catalysts, and equipment employed. Typically, a temperature of from about 500, or from about 700, up to about 1000 or up to about 1200° C., and a pressure of from about 1 atmosphere up to about 3, or up to about 5, or up to about 10, or up to about 20 atmospheres may be employed to produce the liquid $C_2$-$C_{10}$ product that may comprise ethylene, benzene, naphthalene, or a mixture thereof and hydrogen. In some embodiments the $C_1$-$C_3$ alkane is heated by burning a fuel outside the tubes in fuel burning nozzles configured to transfer heat from the burning through the tubes. As described below, the hydrogen produced may be used as the fuel in the fuel burning nozzles outside the tubes.

Catalyst

The catalyst composition, form, size, shape, and properties may vary depending upon such parameters as the reactants, reactor type, tube size and shape, reaction conditions, and/or desired products. In some embodiments the catalyst comprises substantially cylindrical pellets. The catalyst pellets may comprise one or more holes passing through the length of the pellet, may be domed shaped on the ends, and/or may comprise a plurality of grooves on the pellet surface. Suitable catalyst pellets are described in, for example, U.S. publication US2021/0115341 to Sampath which published on Apr. 22, 2021 and is incorporated by reference herein.

In some embodiments the aspect ratio (ratio of height to diameter or cross-section length) of catalyst pellets may be at least 0.3, or at least 0.5 up to about 3, or up to about 2. In some embodiments the catalyst may comprise catalyst pellets of from about 0.5 to about 1.0, or to about 2.0 inches in diameter. In some embodiments the catalyst pellets are substantially cylindrical and wherein at least a portion of the pellets comprise one or more holes passing through the length of the pellet. The holes passing through the catalyst pellets assist in increasing the external surface area and hence generally decrease the characteristic length of the catalyst pellets to ensure adequate mass transfer rate. It may be desirable to have a characteristic length, defined as the pellet volume divided by the external surface area, to be smaller than 0.3, or smaller than 0.2, or smaller than 0.15 cm. With adequate porosity and pore structure the effective diffusivity for light hydrocarbons may be in the range of $5\times10^{\wedge}-3$ to $2\times10^{\wedge}-2$ cm$^2$/s, and the catalyst effectiveness factor may be in the range of from 0.05, or from 0.1 up to 0.5, or up to 0.4.

The catalyst may comprise washcoated honeycomb monolith catalyst or metal monolith in some embodiments. The monolith may comprise ceramic, silica, quartz, glass, metal, silicon carbide, silicon nitride, boron nitride, a metal oxide or any combination thereof. Suitable metal oxides may comprise titania, iron oxide, zirconia, a mixed metal oxide, or any combination thereof.

Reactor Tubes

Like the catalyst, the tubes in the reactor may vary in shape, size, material, and/or properties depending upon such parameters as the reactants, reactor type, reaction conditions, and/or desired products. The plurality of tubes may comprise a ceramic, a metal, or a mixture thereof. Suitable metals may include, for example, alloy 800, alloy 800/HT, alloy 309, any other metallurgy suitable for high temperature services, or a mixture thereof.

In some embodiments the tubes are configured to minimize or lessen pressure drop. For example, the tubes may be configured such that a pressure drop within the plurality of tubes comprises less than about 45 psig.

If desired the plurality of tubes may comprise one or metal inserts within the plurality of tubes to facilitate the transfer of heat in a radial direction within the plurality of tubes. The metal insert may comprise a screen, a plate, or a combination thereof.

In this manner the effective thermal conductivity in a radial direction may be from about 5 to about 200 W/mK while the temperature drop may be less than 50 to 200° C. The plurality of tubes may also be configured such that the heating duty per tube is from about 2 kW/m$^2$ tube to about 70 kW/m$^2$-tube. The size of the tubes may vary depending upon the desired heat transfer and other properties of the system. In some embodiments, a majority of the plurality of tubes within the vessel have a diameter of from about 1, or from about 2 up to about 6, or up to about 7 inches. In some embodiments, one or more of the plurality of tubes within the vessel may have a diameter of from about 1, or from about 2 up to about 6, or up to about 7 inches.

Generally, the reactor comprises fuel burning nozzles outside and along the length of the plurality of tubes in order to burn fuel outside the plurality of tubes. The fuel is not particularly critical so long as it is capable of heating the tubes adequately. In some embodiments the fuel comprises a hydrocarbon, hydrogen, or a mixture thereof. In some embodiments the fuel may comprise hydrogen formed in the process. In some embodiments at least a portion of the heat used in heating the $C_1$-$C_3$ alkane in the tubes comprises heat from a flue gas generated during a catalyst regeneration.

FIG. 1 shows reaction temperature, pressure, and equilibrium conversion for a methane to benzene reaction according to the above embodiments.

Figure 2:
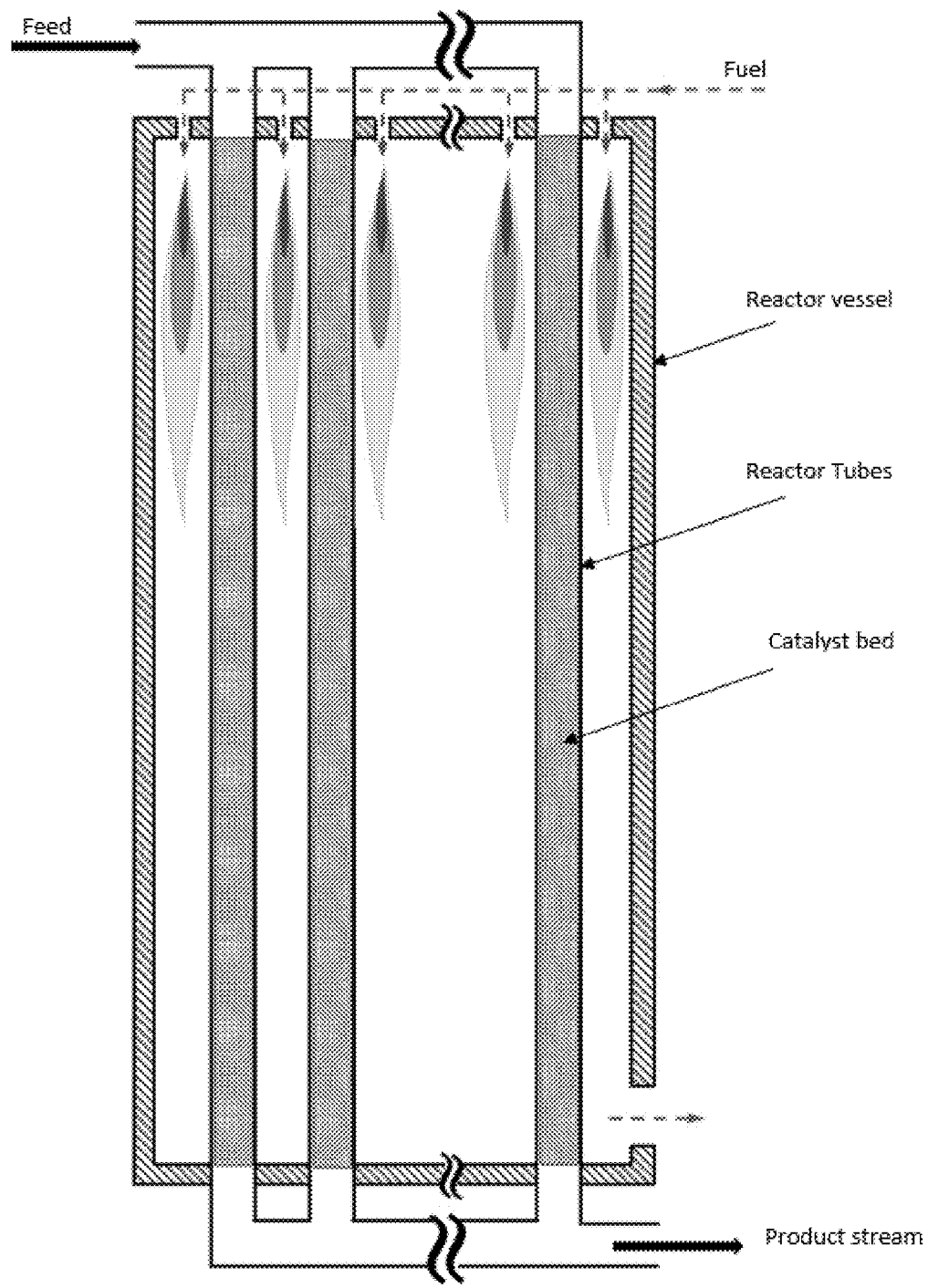
FIG. 2 shows a representative multi-tube reactor with top fired heater.

FIG. 2 shows a representative multi-tube reactor with top fired heater. In this embodiment feed enters the tube from the top and passes over the catalyst in the tubes. The tubes comprising catalyst and feed are heated using fuel burning adjacent or near the tubes. The product of the catalytic reaction exits at the bottom of the reactor.

In the preceding specification, various embodiments have been described with references to the accompanying drawings. It will, however, be evident that various modifications and changes may be made thereto, and additional embodiments may be implemented, without departing from the broader scope of the invention as set forth in the claims that follow. The specification and drawings are accordingly to be regarded as an illustrative rather than restrictive sense.

We claim:

1. A process for converting a $C_1$-$C_3$ alkane to a $C_2$-$C_{10}$ product and hydrogen wherein the process comprises:
    flowing the $C_1$-$C_3$ alkane through a plurality of tubes within a vessel wherein the tubes house a catalyst for converting the $C_1$-$C_3$ alkane to the $C_2$-$C_{10}$ product and hydrogen; and
    heating the $C_1$-$C_3$ alkane under suitable conditions to produce the $C_2$-$C_{10}$ product and hydrogen;
    wherein the $C_1$-$C_3$ alkane is heated by burning a fuel outside the tubes in fuel burning nozzles configured to transfer heat from the burning through the tubes;
    wherein the catalyst comprises cylindrical pellets; and
    wherein at least a portion of the pellets comprise one or more holes passing through the length of the pellet, are domed shaped on the ends, comprise a plurality of grooves on the pellet surface, and have an aspect ratio of at least 0.5 up to about 2.

2. The process of claim 1 wherein the $C_1$-$C_3$ alkane is derived from natural gas.

3. The process of claim 1 wherein the $C_2$-$C_{10}$ product comprises ethylene, benzene, naphthalene, or a mixture thereof.

4. The process of claim 1 further comprising employing one or more metal inserts within the plurality of tubes to facilitate the transfer of heat in a radial direction within the plurality of tubes.

5. The process of claim 1 wherein the fuel comprises a hydrocarbon, hydrogen, or a mixture thereof.

6. The process of claim 5 wherein at least a portion of the fuel comprises hydrogen formed in the process.

7. The process of claim 1 wherein at least a portion of the heat used in heating the $C_1$-$C_3$ alkane comprises heat from a flue gas generated during a catalyst regeneration.

8. The process of claim 1 wherein a pressure drop within the plurality of tubes comprises less than about 45 psig.

9. The process of claim 1 wherein a majority of the plurality of tubes within the vessel have a diameter of from about 2 to about 6 inches.

10. The process of claim 1 wherein the catalyst comprises catalyst pellets of from about 0.5 to about 1.0 inches in diameter.

11. The process of claim 1 wherein the catalyst comprises a washcoated honeycomb monolith catalyst wherein the washcoated monolith catalyst comprises ceramic, silica, quartz, glass, metal, silicon carbide, silicon nitride, boron nitride, a metal oxide or any combination thereof.

12. The process of claim 11 wherein the metal oxide comprises titania, iron oxide, zirconia, a mixed metal oxide, or any combination thereof.

13. The process of claim 1 wherein the catalyst comprises metal monolith.

14. The process of claim 1 wherein the catalyst has a catalyst effectiveness factor of from about 0.05 to about 0.5.

15. A process for converting natural gas to a $C_2$-$C_{10}$ product comprising ethylene, benzene, naphthalene, or a mixture thereof and hydrogen wherein the process comprises:

flowing the natural gas through a plurality of tubes within a vessel wherein the tubes house a catalyst for converting the natural gas to the $C_2$-$C_{10}$ product comprising ethylene, benzene, naphthalene, or a mixture thereof and hydrogen; and heating the natural gas at a temperature of from about 700 to about 1000° C. and a pressure of from about 1 to about 3 atmospheres to produce the $C_2$-$C_{10}$ product comprising ethylene, benzene, naphthalene, or a mixture thereof and hydrogen;

wherein the natural gas is heated by burning a fuel outside the tubes in fuel burning nozzles configured to transfer heat from the burning through the tubes;

wherein the catalyst comprises cylindrical pellets; and wherein at least a portion of the pellets comprise one or more holes passing through the length of the pellet, are domed shaped on the ends, comprise a plurality of grooves on the pellet surface, and have an aspect ratio of at least 0.5 up to about 2.

\* \* \* \* \*